US005608145A

United States Patent [19]
Schroeder et al.

[11] Patent Number: 5,608,145
[45] Date of Patent: Mar. 4, 1997

[54] HIGH-AFFINITY POTASSIUM UPTAKE TRANSPORTER FROM HIGHER PLANTS

[75] Inventors: Julian I. Schroeder, La Jolla, Calif.; Daniel P. Schachtman, Klemzig, Australia

[73] Assignee: The Regents of the University of California, Oakland, Calif.

[21] Appl. No.: 294,872

[22] Filed: Aug. 23, 1994

[51] Int. Cl.$^6$ ............... C12N 15/09; C12N 15/29; A01H 1/00; A01H 5/00
[52] U.S. Cl. ............... 800/205; 800/DIG. 58; 536/23.6; 536/24.1
[58] Field of Search ............... 800/200, 205, 800/250, DIG. 58; 435/172.1, 172.3; 536/23.6, 24.1

[56] References Cited

U.S. PATENT DOCUMENTS 5,139,954  8/1992  Litts et al. ............... 435/320.1

OTHER PUBLICATIONS

Schroeder, J., et al., "Voltage dependence of K+ channels in guard–cell protoplasts," *Proc. Natl. Acad. Sci. USA*, vol. 84, pp. 4108–4112 (Jun. 1987).

Schroeder, J. and Fang, H., "Inward–rectifying K+ channels in guard cells provide a mechanism for low–affinity K+ uptake," *Proc. Natl. Acad. Sci. USA*, vol. 88, pp. 11583–11587 (Dec. 1991).

Fernando, M., et al., "DeNovo Synthesis of Plasma Membrane and Tonoplast Polypeptides of Barley Roots During Short–Term K+ Deprivation," *Plant Physiol.*, vol. 100, pp. 1269–1276 (1992).

Sheahan, J., et al., "Cesium–insensitive mutants of *Arabidopsis thaliana*", *The Plant Journal*, vol. 3(5), pp. 647–656 (1993).

Gaber et al. 1988. Molecular and Cellular Biology, 8(7):2848–2859.

Fernando et al. 1992. Plant Physiol 100:1269–1276.

Vasil et al. 1992. Bio/Technology, 10:667–674.

Hamilton et al. 1990. Nature 346:284–287.

Potrykus 1991. Annu. Res. Plant Physiol. Mol. Biol. 42:205–225.

*Primary Examiner*—Erich E. Veitenheimer
*Attorney, Agent, or Firm*—Townsend and Townsend and Crew LLP

[57] ABSTRACT

The present invention provides polynucleotide sequences encoding high affinity potassium uptake transporters. The polynucleotides of the invention can be used to modulate alkali metal uptake in plants and other organisms.

22 Claims, 3 Drawing Sheets

HIGH-AFFINITY POTASSIUM UPTAKE TRANSPORTER FROM HIGHER PLANTS

This invention was made with Government support under Grant No. MCB 90-04977, awarded by the National Science Foundation. The Government has certain rights in this invention.

BACKGROUND OF THE INVENTION

The present invention relates to isolation and use of genes important in plant nutrition. In particular, it relates to polynucleotides encoding high affinity potassium uptake transporters, recombinant constructs comprising the polynucleotides, and transgenic organisms comprising the polynucleotides.

Potassium (K+) is the most abundant cation in higher plants and plays vital roles for plant nutrition, growth, tropisms, enzyme homeostasis and osmoregulation. Epstein et al., *Proc. Natl. Acad. Sci. USA* 49:684–692 (1963); Kochian et al., *Adv. Botany Res.* 15:93–177 (1988); and Schroeder et al., *Annu. Rev. Biophys. Biomol. Struct.* 23:441–471 (1994). Potassium accumulation can be rate-limiting for agricultural production. $K^+$-uptake from soils into roots is largely mediated by high-affinity $K^+$-uptake ($K_m \approx 10$–$40$ $\mu M$). Newman et al. *Plant Physiol.* 84:1177–1184 (1987); Fernando et al., *Plant Physiol.* 100:1269–1276 (1992); and Maathuis et al. *Planta* 191:302–307 (1993). While potassium channels allow low-affinity potassium-uptake (Schroeder et al., *Proc. Natl. Acad. Sci. USA* 84:4108–4112 (1987); Schroeder et al., *Proc. Natl. Acad. Sci. USA* 88:11583–11587 (1991)), the prior art has yet to elucidate the transport mechanism and structure of the high-affinity potassium nutrition pathway.

High salt levels in soils and the ensuing sodium (Na+) influx into plants severely reduce agricultural production, with ≈30% of irrigated soils being affected by high salt concentrations worldwide. Greenway et al., *Annu. Rev. Plant Physiol.* 31:149–190 (1980). The molecular mechanisms of Na+-uptake into plants remain unknown. It is known, however, that $K^+$ strongly competes with both $Na^+$-and $Cs^+$-uptake and $Cs^+$ toxicity in plant root. Rains et al., *Science* 148:1611 (1965); Welch et al., *Proc. Natl. Acad. Sci. USA* 61:447–453 (1968); and Sheehan et al., *Plant J.* 3:647–656 (1993). Thus, information about potassium transporters may be useful in developing plant varieties tolerant of environmental stresses associated with alkali metal toxicities.

Because of its importance to plant nutrition, the isolation and characterization of genes encoding plant proteins involved in potassium uptake would be extremely useful in the engineering of various crop plants. In addition, expression of such genes could be modified as necessary to provide other advantages, such as salt tolerance. The present invention addresses these and other needs.

SUMMARY OF THE INVENTION

The present invention provides polynucleotides encoding high affinity potassium uptake transporters useful for modulating cation uptake in transgenic organisms. The genes of the invention can be isolated from a number of plant species. The exemplified gene (HKT1) is isolated from wheat (SEQ. ID. No. 1.). The polynucleotide sequences of the genes of the invention are substantially identical to a sequence of least about 50 nucleotides from SEQ. ID. No. 1. Preferred polynucleotides encode a polypeptide having a sequence as shown in SEQ. ID. No. 2.

The invention also provides recombinant expression cassettes comprising a promoter sequence operably linked to a polynucleotide encoding a high affinity potassium uptake transporter. In some embodiments, the polynucleotide is operably linked to the promoter sequence in an antisense orientation to inhibit expression of the endogenous gene. In other embodiments the polynucleotide is operably linked to the promoter sequence in a sense orientation to enhance expression of the transporter. The promoter sequence used may be either constitutive or inducible.

The invention further provides plants comprising a heterologous recombinant expression cassette comprising a plant promoter sequence operably linked to a polynucleotide encoding a high affinity potassium uptake transporter. The plant is typically a flowering plant, such as wheat.

The invention provides methods of modulating alkali metal uptake in plants. The methods comprise introducing into the plant a recombinant expression cassette comprising a promoter sequence operably linked to a polynucleotide encoding a high affinity potassium uptake transporter. The polynucleotide may operably linked to the promoter sequence in an antisense orientation, if inhibition of uptake is desired. Alternatively, the polynucleotide may be operably linked to the promoter sequence in a sense orientation, if enhanced gene expression is desired.

Definitions

The term "alkali metal" refers to elements of the first group of the periodic system: Li, Na, K, Rb, Cs, and Fr. Sodium (Na), potassium (K), and cesium (Cs) are the most important of these elements in plant nutrition. These elements primarily exist as cations in soil and plant cells.

A "high affinity potassium uptake transporter" is a transmembrane plant protein which mediates uptake of potassium and other cations into plant cells. The affinity of such proteins for $K^+$, expressed as $K_m$ is between about 10 and about 40 $\mu M$. The amino acid sequence of an exemplary transporter isolated from wheat (HKT1) is provided here.

A "polynucleotide sequence encoding a high affinity potassium uptake transporter" is a subsequence or full length sequence of a gene, such as the HKT1 gene, which, when present in a transgenic plant has the desired effect, for example, enhancing potassium uptake or inhibiting expression of the endogenous gene. In the case of both expression of transgenes and inhibition of endogenous genes (e.g., by antisense, or sense suppression) one of skill will recognize that the inserted polynucleotide sequence need not be identical and may be "substantially identical" to a sequence of the gene from which it was derived. As explained below, these variants are specifically covered by this term.

In the case where the inserted polynucleotide sequence is transcribed and translated to produce a functional polypeptide, one of skill will recognize that because of codon degeneracy a number of polynucleotide sequences will encode the same polypeptide. These variants are specifically covered by the above term. In addition, the term "polynucleotide sequence encoding a high affinity potassium uptake transporter" specifically includes those full length sequences substantially identical (determined as described below) with the gene sequence disclosed here (SEQ. ID. No. 1) and that encode proteins that retain the function of the high affinity potassium uptake transporter as determined in the in vitro uptake assays described below.

Two nucleic acid sequences or polypeptides are said to be "identical" if the sequence of nucleotides or amino acid residues, respectively, in the two sequences is the same when aligned for maximum correspondence as described below. The term "complementary to" is used herein to mean that the complementary sequence is identical to all or a portion of a reference polynucleotide sequence.

Sequence comparisons between two (or more) polynucleotides or polypeptides are typically performed by comparing sequences of the two sequences over a "comparison window" to identify and compare local regions of sequence similarity. A "comparison window", as used herein, refers to a segment of at least about 20 contiguous positions, usually about 50 to about 200, more usually about 100 to about 150 in which a sequence may be compared to a reference sequence of the same number of contiguous positions after the two sequences are optimally aligned.

Optimal alignment of sequences for comparison may be conducted by the local homology algorithm of Smith and Waterman *Adv. Appl. Math.* 2:482 (1981), by the homology alignment algorithm of Needleman and Wunsch *J. Mol. Biol.* 48:443 (1970), by the search for similarity method of Pearson and Lipman *Proc. Natl. Acad. Sci. (U.S.A.)* 85:2444 (1988), by computerized implementations of these algorithms (BLAST, GAP, BESTFIT, FASTA, and TFASTA in the Wisconsin Genetics Software Package, Genetics Computer Group (GCG), 575 Science Dr., Madison, Wis.), or by inspection.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has at least 60% sequence identity, preferably at least 80%, more preferably at least 90% and most preferably at least 95%, compared to a reference sequence using the programs described above (preferably BLAST) using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 40%, preferably at least 60%, more preferably at least 90%, and most preferably at least 95%.

Another indication that nucleotide sequences are substantially identical is if two molecules hybridize to each other under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions for a Southern blot protocol involve washing at 65° C. with 0.2×SSC.

As used herein, a homolog of a particular high affinity potassium uptake transporter gene (e.g. the wheat HKT1 gene) is a second gene (either in the same plant type or in a different plant type) which has a polynucleotide sequence of at least 50 contiguous nucleotides which are substantially identical (determined as described above) to a sequence in the first gene. It is believed that, in general, homologs share a common evolutionary past.

The phrases "nucleic acid sequence or polynucleotide sequence" refer to a single or double-stranded polymer of deoxyribonucleotide or ribonucleotide bases read from the 5' to the 3' end. The terms include both self-replicating plasmids, infectious polymers of DNA or RNA and non-functional DNA or RNA.

The term "promoter" refers to a region of DNA upstream from the start of transcription and involved in recognition and binding of RNA polymerase and other proteins to initiate transcription. A "plant promoter" is a promoter capable of initiating transcription in plant cells.

The term "plant" includes whole plants, plant organs (e.g., leaves, stems, roots, etc.), seeds and plant cells and progeny of same. The term refers to seed plants, particularly flowering plants, including both monocotyledonous and dicotyledonous plants, as well as other non-seed plants such as algae.

A "heterologous sequence" is one that originates from a foreign species, or, if from the same species, is substantially modified from its original form (e.g., linked to a promoter sequence in an antisense orientation).

BRIEF DESCRIPTION OF THE DRAWINGS

FIGS. 1A–1D show high-affinity $K^+$-uptake and selectivity of HKT1 in yeast and Xenopus oocytes. FIG. 1D shows HKT1-mediated ionic conductivity ratios (±SD). Currents carried by each cation were compared to the $K^+$ current and measured relative to background currents before cation exposures.

DESCRIPTION OF THE PREFERRED EMBODIMENT

The present invention provides polynucleotide sequences encoding polypeptides which confer potassium uptake. In particular, the present disclosure describes the isolation and characterization of a gene encoding a high affinity potassium uptake transporter in wheat (HKT1). The substrate-affinity, saturation and cation selectivity of the exemplary protein described here correspond to hallmark properties of classical high-affinity potassium uptake in plants. Rains et al., *Science* 148:1611 (1965).

Isolation of the HKT1 gene allows one of skill to readily isolate homologous genes in wheat and other plant species. The polynucleotides of the invention can then be used to modulate alkali metal uptake in plants and other organisms. For instance, the polynucleotides can be used to enhance potassium uptake in transgenic cultivars of economically important plant species. Such plants are particularly useful for growing in potassium-deficient soils. Alternatively, the sequences can be used to inhibit expression of the transporters and thereby inhibit alkali metal uptake. Such plants are useful where toxic levels of alkali metals are present. Other uses of the polynucleotides include the transformation of microorganisms and plants for use in removing alkali metals, heavy metals, or other cations from soils or water.

I. Preparation of Polynucleotides of the Invention

Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et at., *Molecular Cloning - A Laboratory Manual,* Cold Spring Harbor Laboratory, Cold Spring Harbor, N.Y., (1989).

Based on the HKT1 nucleic acid sequence provided below, one of skill can design oligonucleotide probes to identify high affinity potassium uptake transporter genes in a cDNA or genomic DNA library prepared from plant DNA. To construct genomic libraries, large segments of genomic DNA are generated by random fragmentation, e.g. using restriction endonucleases, and are ligated with vector DNA to form concatemers that can be packaged into the appropriate vector. To prepare a cDNA library, mRNA is isolated from the desired organ, such as a flower, and a cDNA library which contains the target gene transcript is prepared from the mRNA. Alternatively, cDNA may be prepared from mRNA extracted from other tissue types (organs) in which transporter genes or homologs are expressed such as roots or leaves.

The cDNA or genomic library can then be screened using a probe based upon the sequence of a cloned gene such as that shown in SEQ. ID. No. 1. Probes may be used to hybridize with genomic DNA or cDNA sequences to isolate homologous genes in the same or different plant species. The use of such hybridization techniques for identifying homologous genes is well known in the art and need not be described further.

Alternatively, polynucleotides may be synthesized by well-known techniques as described in the technical literature. See, e.g., Carruthers et at., *Cold Spring Harbor Symp. Quant. Biol.* 47:411–418 (1982), and Adams et at., *J. Am. Chem. Soc.* 105:661 (1983). Double stranded DNA fragments may then be obtained either by synthesizing the complementary strand and annealing the strands together under appropriate conditions, or by adding the complementary strand using DNA polymerase with an appropriate primer sequence.

II. Modulation of Alkali Metal Uptake

The isolated sequences prepared as described herein, can be used in a number of techniques to modulate alkali metal uptake in transgenic organisms. As noted above, the polynucleotides of the invention can be introduced into plants and used to increase potassium uptake in plants grown in potassium deficient soils.

One of skill will recognize that the polypeptides encoded by the genes of the invention, like other proteins, have different domains which perform different functions. Thus, the high affinity potassium uptake transporter gene sequences need not be full length, so long as the desired functional domain of the protein is expressed. Modified protein chains can also be readily designed utilizing various recombinant DNA techniques well known to those skilled in the art. For example, the chains can vary from the naturally occurring sequence at the primary structure level by amino acid substitutions, additions, deletions, and the like. These modifications can be used in a number of combinations to produce the final modified protein chain.

In general, modifications of the sequences encoding high affinity potassium uptake transporters may be readily accomplished by a variety of well-known techniques, such as site-directed mutagenesis (see, Kunkel, *Proc. Natl. Acad. Sci. USA* 82:488–492 (1985); Gillman and Smith, *Gene* 8:81–97 (1979) and Roberts, S. et al., *Nature* 328:731–34 (1987)). In addition, seeds or other plant material can be treated with a mutagenic chemical substance, according to standard techniques. Such chemical substances include, but are not limited to, the following: diethyl sulfate, ethylene imine, ethyl methanesulfonate and N-nitroso-N-ethylurea. Alternatively, ionizing radiation from sources such as, for example, X-rays or gamma rays can be used.

Mutations can be introduced into the protein to alter any characteristic of the transporter protein. For instance, the affinity of the transporter for potassium and/or other cations can be altered. Thus, the affinity for particular ions can be altered to affect the uptake of particular cations and render the proteins either more or less selective. In particular, the transporters can be rendered more selective for potassium, thereby increasing potassium uptake in transgenic plants. Alternatively, for applications in which a transgenic organisms are used to remove toxic cations (e.g., alkali metals or heavy metals), selectivity can be increased for a particular target element.

One of ordinary skill will appreciate that the effect of many mutations can easily be determined using routine in vitro assays. The effect of mutations or the alteration of gene expression is conveniently detected by measuring the increase or decrease of uptake of alkali metals by the transformed plant or cells isolated from it. For instance, tracer analogues of $K^+$, such as $^{86}Rb^+$, can be used to measure uptake characteristics of transformed plants. Suitable methods for carrying out such assays are described in detail below.

Mutations can also evaluated using transgenic yeast comprising the mutated gene. Methods for production of transgenic yeast expressing the genes of the invention are described below. The transgenic yeast can be cultured in a medium containing high levels of desired cation (e.g., sodium). Transgenic yeast comprising mutant transporters with decreased affinity for the cation are identified by their ability to proliferate in the medium. Genes with low affinity for sodium identified in this manner can be used to produce salt tolerant plant cultivars. Mutant transporters with increased affinity for a toxic cation (e.g., sodium, cesium, or heavy metals such as Pb or Cd) can also be identified using, for instance, replica plating. Transgenic organisms comprising such genes can be used to remove toxic heavy metals or alkali metals from soils or water.

Transgenic organisms comprising high affinity potassium uptake transporter polynucleotide sequences can also be used to preferentially take up alkali metals from the environment. For instance, such organisms can be used to reduce levels of sodium or cesium in soil or water. A wide variety of organisms can be used for these purposes, including microorganisms, e.g., bacteria, yeast, or fungi. For instance, transgenic plants can be used to remove sodium from water or soil with high levels of sodium chloride or other salts. Such transgenic plants, in particular plants tolerant of high salt levels such as algae or halophytic flowering plants, are thus conveniently used for desalinization of sea water.

The polynucleotide sequences of the invention can also be used to inhibit uptake of alkali metals, such as sodium or cesium, which may be at toxic levels in the soil or water. Techniques suitable for inhibiting gene expression in plants are summarized briefly below.

For instance, antisense technology can be conveniently used to inhibit high affinity potassium uptake transporter gene expression. To accomplish this, a nucleic acid segment from the desired gene is cloned and operably linked to a promoter such that the anti-sense strand of RNA will be transcribed. The construct is then transformed into plants and the antisense strand of RNA is produced. In plant cells, it has been shown that antisense RNA inhibits gene expression by preventing the accumulation of mRNA which encodes the enzyme of interest, see, e.g., Sheehy et at., *Proc. Nat. Acad. Sci. USA,* 85:8805–8809 (1988), and Hiatt et at., U.S. Pat. No. 4,801,340.

The nucleic acid segment to be introduced generally will be substantially identical to at least a portion of the endogenous high affinity potassium uptake transporter gene or genes to be repressed. The sequence, however, need not be perfectly identical to inhibit expression. The vectors of the present invention can be designed such that the inhibitory effect applies to other proteins within a family of genes exhibiting homology or substantial homology to the target gene. For instance, segments from a high affinity potassium uptake transporter gene from wheat can be used to inhibit expression of homologous genes in different plant species. The introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments will be equally effective. Normally, a sequence of between about 30 or 40 nucleotides and about 2000 nucleotides should be used, though a sequence of at least about 100 nucleotides is preferred, a sequence of at least about 200 nucleotides is more preferred, and a sequence of at least about 500 nucleotides is especially preferred.

Another method of suppression is sense suppression. Introduction of nucleic acid configured in the sense orientation has been recently shown to be an effective means by which to block the transcription of target genes. For an example of the use of this method to modulate expression of endogenous genes see, Napoli et al., *The Plant Cell* 2:279–289 (1990), and U.S. Pat. No. 5,034,323.

As with antisense suppression, the introduced sequence need not be identical to the endogenous sequence but may be substantially identical to the gene. This minimal identity will typically be greater than about 65%, but a higher identity might exert a more effective repression of expression of the endogenous sequences. Substantially greater identity of more than about 80% is preferred, though about 95% to absolute identity would be most preferred. As with antisense regulation, the effect should apply to any other proteins within a similar family of genes exhibiting homology or substantial homology.

The introduced sequence, needing less than absolute identity, also need not be full length, relative to either the primary transcription product or fully processed mRNA. A higher identity in a shorter than full length sequence compensates for a longer, less identical sequence. Furthermore, the introduced sequence need not have the same intron or exon pattern, and identity of non-coding segments will be equally effective. Normally, a sequence of the size ranges noted above for antisense regulation is used.

Catalytic RNA molecules or ribozymes can also be used to inhibit expression of high affinity potassium uptake transporter genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs. The design and use of target RNA-specific ribozymes is described in Haseloff et al. *Nature,* 334:585–591 (1988).

III. Construction of Recombinant Vectors

To use isolated sequences encoding high affinity potassium uptake transporters in the above techniques, recombinant DNA vectors suitable for transformation of plants and other organisms are prepared. Generally, a polynucleotide sequence coding for the desired high affinity potassium uptake transporter polypeptide, for example a cDNA sequence encoding a full length protein, will be combined with transcriptional and translational initiation regulatory sequences which will direct the transcription of the sequence from the gene in the transgenic organisms.

Expression of heterologous proteins in yeast is well known and described, for instance, in *Methods in Yeast Genetics,* Sherman, F., et al., Cold Spring Harbor Laboratory, (1982). A number of well known yeast expression plasmids can be used as vectors. A gene of interest can be fused to any of the promoters in various yeast vectors. For instance, suitable vectors are described in the literature (Botstein, et al., 1979, Gene, 8:17–24; Broach, et al., 1979, Gene, 8:121–133).

Techniques for transforming other fungi are well known in the literature, and have been described, for instance, by Beggs (*Nature* 275:104–108 (1978)), Hinnen et al. (*Proc. Natl. Acad. Sci. USA* 75:1929–1933, 1978), Yelton et al. (*Proc. Natl. Acad. Sci. USA* 81:1740–1747, 1984), Russell (*Nature* 301:167–169, 1983) and U.S. Pat. No. 4,935,349.

For expression in higher plants, a plant promoter fragment may be employed which will direct expression of the transporter in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'- promoter derived from T-DNA of *Agrobacterium turnafaciens,* and other transcription initiation regions from various plant genes known to those of skill.

Alternatively, the plant promoter may direct expression of the gene in a specific tissue or may be otherwise under more precise environmental or developmental control. Such promoters are referred to here as "inducible" promoters. Examples of environmental conditions that may effect transcription by inducible promoters include anaerobic conditions or the presence of light.

Examples of promoters under developmental control include promoters that initiate transcription only in certain tissues, such as roots, fruit, seeds, or flowers. Using a particular organ-specific promoter expression of the genes of the invention can be targeted to desired tissues within the plant. For instance, a fruit specific promoter can be used to target expression of the transporters of the invention to fruit, which results in increased levels of alkali metals (e.g., potassium) in the fruit. This application is particularly useful increasing the nutritional value of fruit such as bananas, which are a natural source of potassium. More generally, any tissue within the plant can be used a sink for particular cations by choice of the appropriate inducible promoter. For instance, if transgenic plants are used to remove toxic alkali or heavy metals from water or soil, the metals can be targeted to particular organs to minimize the deleterious effects of the metals.

As noted below, HKT1 gene expression is primarily localized to cortical cells in roots, to cell layers bordering the vascular tissue in leaves, and to leaf sheath cells. Thus, the promoter sequence from the genes of the invention can be used to target expression of high affinity potassium uptake transporter genes or other genes to these tissues. The promoter sequence is readily identified using standard methods and operably linked to the desired structural gene sequence for expression in root cortex or leaf tissue.

If proper polypeptide expression is desired, a polyadenylation region at the 3'-end of the coding region should be included. The polyadenylation region can be derived from the natural gene, from a variety of other plant genes, or from T-DNA.

The vector comprising the sequences from a high affinity potassium uptake transporter gene will typically comprise a marker gene which confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosluforon or Basta.

IV. Plant Transformation and Regeneration

Techniques for transforming a wide variety of higher plant species are well known and described in the technical and scientific literature. See, for example, Weising et al. *Ann. Rev. Genet.* 22:421–477 (1988).

Recombinant constructs may be introduced into the genome of the desired higher plant host by a variety of conventional techniques. For example, the DNA construct may be introduced directly into the genomic DNA of the plant cell using techniques such as electroporation and microinjection of plant cell protoplasts, or the DNA constructs can be introduced directly to plant tissue using ballistic methods, such as DNA particle bombardment. Alternatively, the DNA constructs are introduced into the plant using *Agrobacterium tumefaciens*.

Microinjection techniques are known in the art and well described in the scientific and patent literature. The introduction of DNA constructs using polyethylene glycol precipitation is described in Paszkowski et al. *Embo J.* 3:2717–2722 (1984). Electroporation techniques are described in Fromm et al. *Proc. Natl. Acad. Sci. USA* 82:5824 (1985). Ballistic transformation techniques are described in Klein et al. *Nature* 327:70–73 (1987).

*Agrobacterium tumefaciens*-meditated transformation techniques are the most commonly used methods for transformation of higher plants. See, for example Horsch et at. *Science* 233:496–498 (1984), and Fraley et at. *Proc. Natl. Acad. Sci. USA* 80:4803 (1983). In theses methods, the DNA constructs are combined with suitable T-DNA flanking regions and introduced into a *Agrobacterium tumefaciens* host vector. The virulence functions of the *Agrobacterium tumefaciens* host will direct the insertion of the construct and adjacent marker into the plant cell DNA when the cell is infected by the bacteria.

Transformed plant cells which are derived by any of the above transformation techniques can be cultured to regenerate a whole plant which possesses the transformed genotype (e.g., increased copy number of the high affinity potassium uptake transporter gene) and thus the desired phenotype (e.g., enhanced potassium uptake). Such regeneration techniques rely on manipulation of certain phytohormones in a tissue culture growth medium, typically relying on a biocide and/or herbicide marker which has been introduced together with the heterologous nucleotide sequences. Plant regeneration from cultured protoplasts is described in Evans et al., *Protoplasts Isolation and Culture, Handbook of Plant Cell Culture,* pp. 124–176, MacMillilan Publishing Company, N.Y., 1983; and Binding, *Regeneration of Plants, Plant Protoplasts,* pp. 21–73, CRC Press, Boca Raton, 1985.

Regeneration can also be obtained from plant callus, explants, organs, or parts thereof. Such regeneration techniques are described generally in Klee et al. *Ann. Rev. of Plant Phys.* 38:467–486 (1987).

The methods of the present invention are particularly useful for incorporating the high affinity potassium uptake transporter genes into transformed plants in ways and under circumstances which are not found naturally. In particular, the high affinity potassium uptake transporter polypeptides may be expressed at times or in quantities which are not characteristic of natural plants.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

The invention has use over a broad range of types of plants, including, for instance, species from the genera Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Hyoscyamus, Lycopersicon, Nicotiana, Solanum, Petunia, Digitalis, Majorana, Helianthus, Lactuca, Bromus, Asparagus, Antirrhinum, Hererocallis, Nemesis, Pelargonium, Panieum, Pennisetum, Ranunculus, Senecio, Salpiglossis, Cucumis, Browaalia, Glycine, Lolium, Musa, Oryza, Zea, Triticum, Sorghum, and Datura. Algal species include members of the genera Chara, Nitella, and Acetabularia.

The following Examples are offered by way of illustration, not limitation.

EXAMPLE 1

This example describes the isolation and characterization of a cDNA encoding a high-affinity potassium transporter from plants. High-affinity potassium-uptake in higher plant roots can be induced when plants are deprived of potassium, for reference see Femando, et al., *Plant Physiol.* 100:1269–1276 (1992) and Drew, et al. *Planta* 160:490–499 (1984). Therefore, to clone a high-affinity potassium-uptake transporter, a cDNA library was constructed using messenger RNA isolated from 4-day old wheat roots (*T. aestivurn*) grown in a medium devoid of potassium. The mutant yeast strain deficient in potassium-uptake, *Saccharomyces cerevisiae* strain CY162 described by Anderson, et al. in *Proc. Natl. Acad. Sci. USA* 89:3736–3740 (1992), was transformed with purified wheat root plasmid cDNAs. Screening the surviving transformants resulted in the isolation of a cDNA, named HKT1. The cDNA allowed the mutant yeast strain to grow on media containing 30 µM $K^+$.

Expression cloning and sequence analysis was done as follows. Poly(A)+mRNA was isolated from roots (0–6 mm from tip) of wheat (*T. aestivum*) cv. Atlas 66) grown in a $K^+$-free medium containing 0.6 mM $CaCl_2$. A size-selected (>1500 bp) unidirectional cDNA library was constructed in the PYES2 plasmid (by Invitrogen Inc., San Diego, Calif.). Yeast strain CY162 was transformed with purified plasmid cDNAs. Those yeast mutants which survived under $K^+$-free conditions were selected and from each were isolated the complementing cDNA using techniques described by Anderson, et al. supra and Frommer, et al., *Proc. Natl. Acad. Sci. USA* 90:5944–5948 (1993). Applying these methods, the cDNA designated HKT1 was isolated and the cloned fragment the plasmid harbored was analyzed further.

Figure 3:
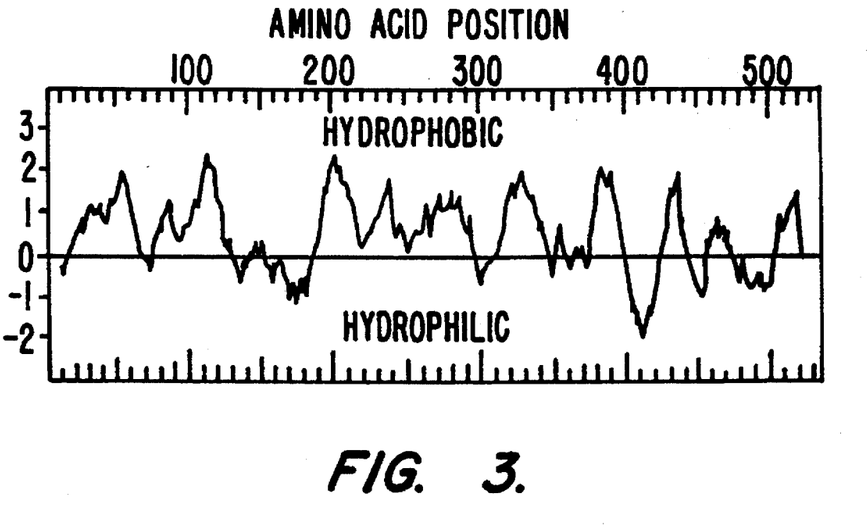
FIG. 3 is a hydropathy plot of HKT1.

Sequence analysis of the double-stranded HKT1 cDNA was done in both directions by the Sequenase protocol supplied by the vendor (USB, Cleveland, Ohio). The HKT1 sequence shown as Seq ID. No.:1 contains an open reading frame encoding a predicted protein of 534 amino acids, Seq ID. No.:2 (molecular mass =58.9 kDa). As shown from the hydrophilicity plot of FIG. 3, the HKT1 protein comprises 10 to 12 putative membrane-spanning domains such as that describe by Kyte, et al., *J. Molec. Biol.* 157:105–132 (1984), which is consistent with its role as a plasma membrane ion transporter. In addition, sequence analysis uncovered no consensus sequences for catalytic ATP binding sites as defined by Higgins, et al. *Nature* 323:448–450 (1986), suggesting that ATP hydrolysis by HKT1 may not be required as an energy source for HKT1-mediated $K^+$-uptake. A search of the non-redundant cDNA database showed a weak similarity (~19% amino acid identity) to potassium uptake transporters (TRKs) from Saccharomyces species in some of the hydrophobic domains described by Ko, et al. *Mol. Cell Biol.* 8:4266–4273 (1991).

HKT1 hybridizes to one DNA band in both *Arabidopsis thaliana* and in a diploid wheat line in which the gene was mapped to chromosome 7 (data not shown). To obtain these results, genomic DNA was isolated from wheat and Arabidopsis and digested with restriction enzymes, size-fractionated and blotted to nylon membrane (Amersham). The membrane was incubated with radiolabelled (Amersham) HKT1 cDNA. After 48 h at 50° C., the filter was washed 3 times at 65° C. in 2×SSC 0.1% SDS and once in 1×SSC 0.1% SDS and then exposed to film for 2 days.

The expression pattern of HKT1 RNA was determined by in situ hybridizations to sections of wheat tissue by the following methods. The HKT1 cDNA was used as a probe after 158 nucleotides including the poly(A)+ tail were removed from the C terminus. Antisense mRNA labeled with $^{35}S$ was synthesized from HKT1 (GC content 47%). Sections were 8 to 10 µM thick. Hybridization conditions were as described by Drews, et al. *Cell* 65:991–1002 (1991). Slides were exposed for 1–2 weeks. A flower specific Arabidopsis gene (CAL) was used as a control (GC content 46%).

HKT1 expression was primarily localized to cortical cells in roots, to cell layers bordering the vascular tissue in leaves, and to leaf sheath cells. HKT1 expression in roots and leaves is consistent with data indicating high-affinity potassium-uptake in several plant tissues as described by Epstein, *Nature* 212:1324–1327 (1966). Expression of HKT1 in the root cortex supports indications that cortical cells have a large potassium-uptake activity during potassium nutrition from soils, Newman, et al., *Plant Physiol.* 84:1177–1184 (1987), and Maathuis, et al., *Planta* 191:302–307 (1993).

EXAMPLE 2

This example describes experiments performed to characterize the potassium uptake properties of the expressed HKT1. The substrate affinity, saturation and cation selectivity of cloned HKT1 was found to correspond to hallmark properties of classical high-affinity potassium uptake in plants described by Epstein, et al., *Proc. Natl. Acad. Sci. USA* 49:684–692 (1963), Epstein, supra, and Rains, et al., *Science* 148, 1611 (1965).

A. Uptake characteristics of yeast complemented with HKT1 cDNA.

Figure 1A:
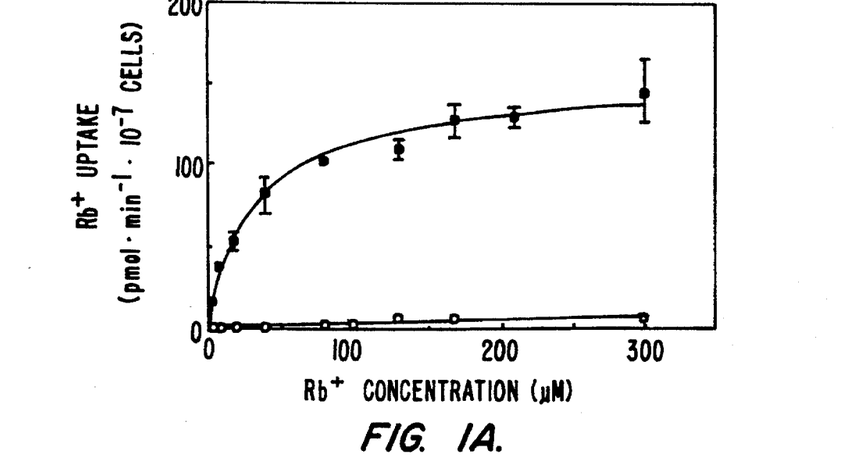
FIG. 1A shows the uptake rate of $^{86}Rb^+$ as a function of $Rb^+$ concentration in a yeast strain deficient in $K^+$ uptake 15 (control: open symbols) and in the same strain expressing HKT1 (closed symbols; Marquardt-Levenberg fit).

The HKT1-expressing *S. cerevisiae* strain CY162 was analyzed using $^{86}Rb^+$ as a tracer analogue for $K^+$ following the methods described by Epstein, supra. The yeast were grown overnight then $K^+$-starved for 6 h, see Anderson, et al. supra. $Rb^+$-uptake rates (calculated relative to O.D. at 600 nm) remained linear for >60 min in CaMES flux buffer, see Rodriguez-Navarro, et al., *J. Gen. Physiol.* 87:649–674 (1986). After 40 rain cells were concentrated on 0.45 µm nylon membrane, washed and analyzed in a Beckman LS-230 liquid scintillation counter. The results of FIG. 1*a* shows the uptake rate of $^{86}Rb^+$ as a function of $Rb^+$ concentration in the yeast strain CY162 deficient in potassium uptake (control: open symbols) and in the same strain expressing HKT1 (closed symbols; Marquardt-Levenberg fit). From this data, the control shows only very low rates of $^{86}Rb^+$-uptake while large $^{86}Rb^+$-uptake rates were evident in the yeast strain expressing the single wheat root HKT1 cDNA. $Rb^+$-uptake rates in HKT1-expressing yeast could be described by a single Michaelis-Menten function which saturated at approximately 300 µM $Rb^+$ and yielded an apparent equilibrium dissociation constant ($K_m$) of 29±6 µM $Rb^+$ (n=4; FIG. 1*a*). These data strongly correlate to high-affinity potassium accumulation in plant roots, which shows an apparent $K_m$ in the range of 10 to 40 µM $Rb^+$ and saturation at approximately 200 µM $Rb^+$ as described by Epstein, supra, Epstein, et al. supra, and Newman, et al. supra.

The biophysical transport mechanism of high-affinity potassium-uptake into higher plant cells remains unknown. Several putative mechanisms have been suggested (reviewed in Kochjan, et al., *Adv. Botany Res.* 15:93–177 (1988), Schroeder, et al., *Annu. Rev. Biophys. Biomiol. Struct.* 23:441–471 (1994) and Poole, *Ann. Rev. Plant Physiol.* 29:437–460 (1978)), including a $K^+$-ATPase, a $K^+$-$H^+$ exchanger (Poole, et al. supra), or a $K^+$-$H^+$ co-uptake transporter, (Rodriguez-Navarro, et al. supra), energized by the proton-extruding ATPase (Spanswick, *Annu. Rev. Plant Physiol.* 32:267–289 (1981)).

Figure 1B:
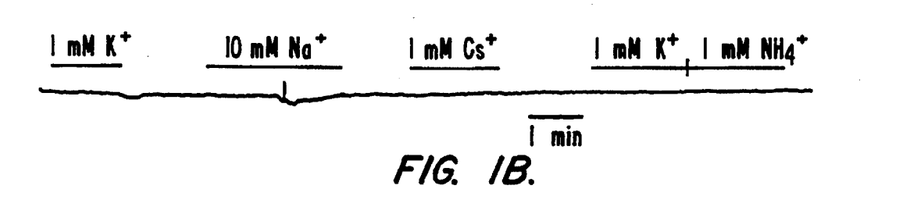
FIG. 1B shows the results when control, water-injected oocytes were exposed to extracellular cations at the indicated times ($V_m$=−60 mV). Current scale is as shown in FIG. 1C.
Figure 1C:
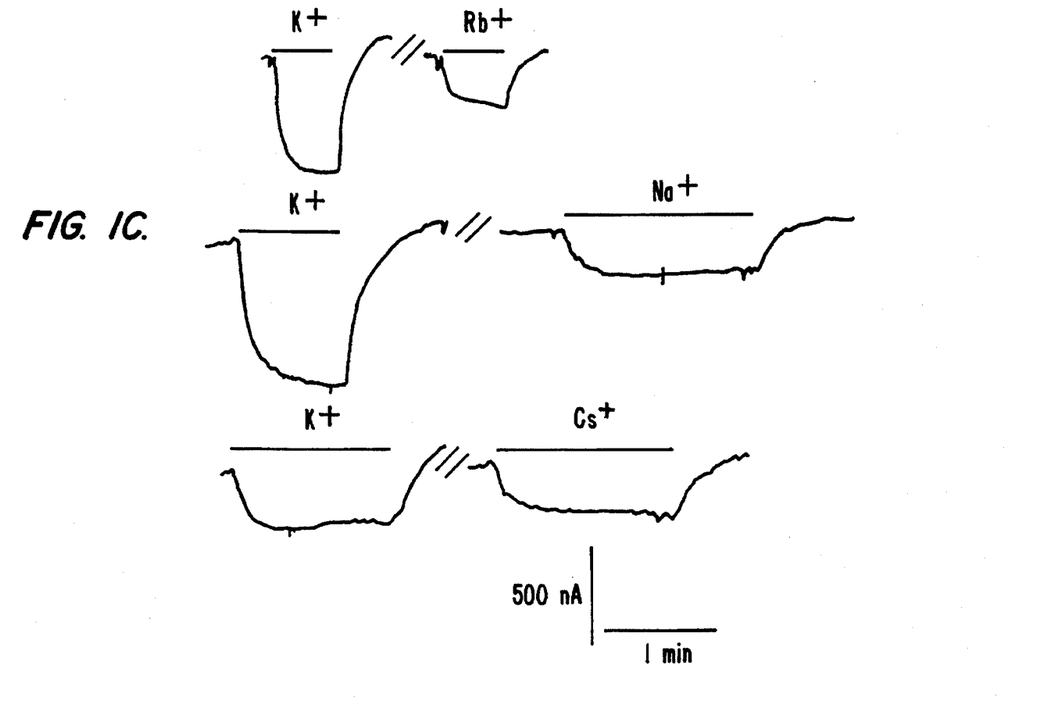
FIG. 1C shows ionic selectivity of HKT1-induced currents in Xenopus oocytes. Changes in ionic currents are shown in 3 HKT1-expressing oocytes in response to extracellular perfusion with (1 mM) $K^+$, $Rb^+$, $Na^+$ and $Cs^+$. Perfusion times are indicated above each trace. Currents induced by 1 mM $K^+$ are shown for reference. Membrane potential was −80 mV ($Na^+$, $Cs^+$), −90 mV ($Rb^+$).
Figure 1D:
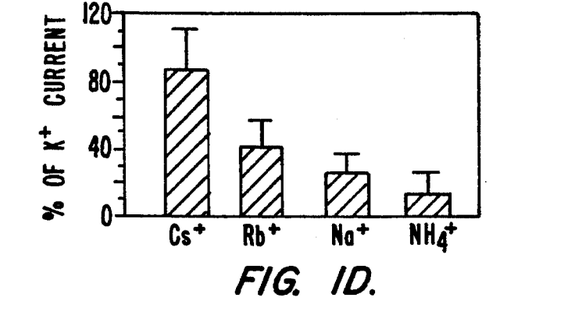
Figure 2A:
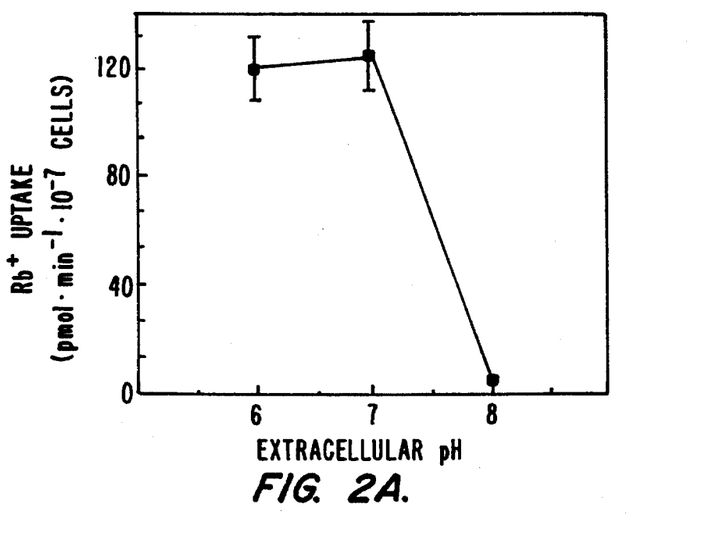
FIGS. 2A and 2B show that uptake rate (2A) and conductance shift (2B) of HKT1 depends on the extracellular pH.

$^{86}Rb^+$-uptake by HKT1-expressing yeast was strongly enhanced by acidification of the extracellular pH from pH 8 to the range from pH 6 to 7, suggesting, proton-coupled $K^+$-uptake (FIG. 2a). For these experiments, the CaMES buffer (Rodriguez-Navarro, et al. supra), was adjusted to pH 7 and 8 with 10 mM HEPES in place of MES (methods FIG. 1; 100 µM $Rb^+$). At pH 8, $Rb^+$-uptake by HKT1 was also larger than in controls with the non-transformed yeast strain.

B. High-affinity potassium uptake and selectivity of HKT1 expressed in Xenopus oocytes.

The functional properties of HKT1-mediated high-affinity potassium-uptake were characterized more directly by expression and voltage clamping of HKT1 in Xenopus oocytes. The results shown in FIGS. 1a, 1b, and 1c were from experiments performed where oocyte mRNA injections (15–20 ng), voltage-clamp recordings, data acquisition and analysis were as described by Schachtman, et al., *Science* 258:1654–1658 (1992). Oocyte bath solutions contained in mM: 1.8 $CaCl_2$, 1 $MgSO_4$, 10 HEPES, pH =7.5, and sorbitol: osmolality 240 mosmol $kg^{-1}$. $K^+$, $Na^+$, $Cs^+$ and $NH_4^+$ were added as glutamate salts, and $Rb^+$ as $Cl^{31}$ salt. Background current measurements before and after perfusions in 1b and 1c contained 1 mM Tris glutamate. Perfusion rate was 2 ml/min (bath volume ~600 µl).

The control results in FIG. 1b were obtained with water-injected oocytes exposed to extracellular cation at the indicated times (Vm=−60 mV). The current scale in 1(b) is the same as that shown in 1c. These control experiments (where n=20) showed no changes in ion currents when water-injected oocytes were perfused with $K^+$ or other cations.

The ionic selectivity of HKT1-induced currents in Xenopus oocytes is shown in 1c. Changes in ionic currents are shown in 3 HKT1-expressing oocytes in response to extracellular perfusion with (1 mM) $K^+$, $Rb^+$, $Na^+$ and $Cs^+$. Perfusion times are indicated above each trace. Currents induced by 1 mM $K^+$ are shown for reference. Membrane potential was −80 mV ($Na^+$, $Cs^+$), −90 mV ($Rb^+$). From these results (where n=95 oocytes, isolated from 16 frogs) it was found that large inward currents developed slowly when HKT1-expressing oocytes were exposed to $K^+$.

HKT1-mediated ionic conductivity ratios (±SD) are shown in FIG. 1d. Currents carded by each cation were compared to the $K^+$ current and measured relative to background currents before cation exposures (as in FIG. 1c). The cation selectivity of HKT1 was characterized by complete replacement of $K^+$ in the oocyte bathing medium with other alkali metal ions and $NH_4^+$. Rubidium-induced currents were 41±15 % as large as $K^+$ currents (±-S.D. n=15; FIG. 1c, d). Sodium (n=19) and $NH_4^+$ ions (n 13) were transported at low rates relative to the potassium-uptake rate (FIG. 1c, d). Cesium was transported efficiently into HKT1-expressing oocytes at ≈86+24 % the rate of $K^+$ ions (n=11; FIG. 1c, d). A selectivity sequence of $K^+>Cs^+>Rb^+>Na^+>NH_4^+$ was estimated from these results (FIG. 1d).

C. Voltage-clamp studies of transport mechanism of high-affinity potassium uptake of HKT1 expressed in Xenopus oocytes, The uptake rate shown in FIG. 2a and conductance shift shown in FIG. 2b of HKT1 depends on the extracellular pH. As described above for FIG. 2a, the extracellular acidification from pH 8 to pH 7 and 6 caused a dramatic enhancement of $Rb^+$-uptake in HKT1-expressing yeast and the further acidification to pH 5.0 and 4.0 reduced the rate of $Rb^+$-uptake when compared to pH 7.0. For the results shown in FIG. 2(b) oocyte background currents (in 1 mM Tris glutamate) were subtracted from currents induced by exposure to I mM $K^+$ glutamate pH=7.5 and 5.5 (solutions: FIG. 1) to obtain the illustrated current-voltage relationships in b and to determine conductance shifts of HKT1-associated currents. Voltage ramps (duration 3's) were applied to oocytes from a holding potential of−60 mV and data were low-pass filtered at 20 Hz. Zero-current potential ($V_0$) shifts were calculated using the equation 19 derived for co-uptake of one $H^+$ per $K^+$ ion: $V_0$=58/2 mV ($\Delta$pH+log ($[K^+]ext/[K^+]cyt$)), where $[K^+]ext$, $[K_{30}]cyt$, and $\Delta$pH are the external and cytoplasmic $K^+$ activities and the pH gradient ($ph_{cyt}$−$ph_{ext}$), respectively. In several experiments upon acidification, HKT1-mediated currents did not reverse with respect to oocyte background current in 1 mM Tris glummate, although current-voltage curves also showed ph-dependent depolarizing shifts.

Figure 2B:
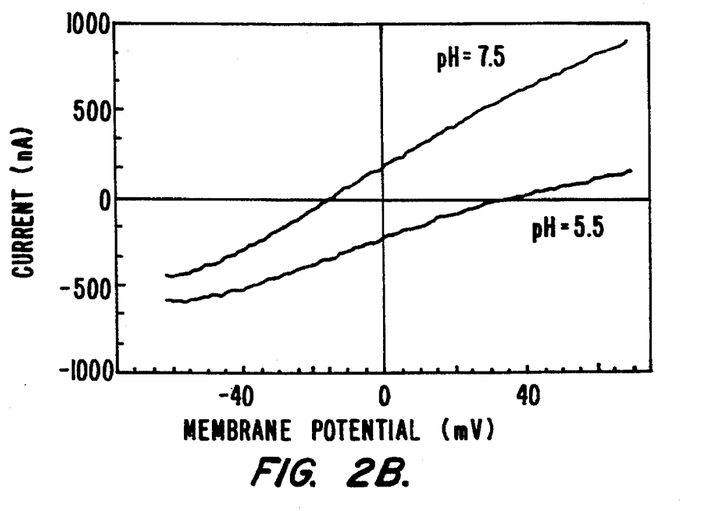

The large currents observed in oocytes expressing HKT1 (FIG. 1c) rule out an electroneutral $K^+$—$H^+$ exchanger as the mechanism of high-affinity $K^+$ accumulation. At depolarized membrane potentials, $K^+$-induced currents were outward (FIG. 2b; n=45 oocytes) and removal of cations resulted in more positive background currents (FIG. 1c), indicating that exposure to extracellular cations may modify oocyte properties and/or partially enhance HKT1 activity. The mechanism of proton-coupling to potassium-uptake was directly investigated by measurements of shifts in the HKT1 conductance (FIG. 2b). In contrast to control oocytes (n=6), acidification by one pH unit in the pH range of 8.5 to 5.5 caused positive shifts in the HKT1-mediated conductance by +24 ±5 mV; acidification by two pH units caused a shift of +58 ±7 mV (n=7; FIG. 2b). Furthermore, increases in the extracellular $K^+$ concentration from 0.5 to 5 mM caused a zero-current potential shift of +22 ±4 mV (n=10). Shifts in the zero-current potential by +29 mV per pH unit acidification (FIG. 2b) or per 10-fold increase in $[K^+]$would be consistent with a stoichiometry of uptake of ≈1 proton per $K^+$ ion by HKT1 (see equation at end of legend to FIG. 2), see Lester, et at., *Ann. Rev. of Pharm. and Toxicol.* 34, 219–249 (1994). However, absolute zero-current potentials varied, possibly because of other conductance properties.

The functional properties of HKT1 provide direct evidence for the classical hypothesis that higher plants possess a high-affinity potassium accumulation pathway which is distinct from low-affinity potassium-uptake transporters 1. Inward-rectifying potassium channels provide one molecular pathway for low-affinity, cell-specific, potassium-uptake, see Schroeder, et.al., *Annu. Rev. Biophys. Biomiol. Struct.* 23, 441–471 (1994), Schroeder, et at., *Proc. Natl. Acad. Sci. USA* 84, 4108–4112 (1987), Schroeder, et at., *Proc. Natl. Acad. Sci. USA* 88, 11583–11587 (1991), Anderson, et al., Proc. Natl. Acad. Sci. USA 89, 3736–3740 (1992), Schachtman, et at., Science 258, 1654–1658 (1992). The electrogenic nature of HKT1-mediated transport (FIG. 1c), the lack of a catalytic ATP-binding domain, as well as the pH dependencies of $Rb^+$-uptake (FIG. 2a) and of HKT1-associated currents (FIG. 2b), together suggest that $K^+$—$H^+$ co-uptake is the biophysical transport mechanism of high-affinity potassium-uptake into higher plant cells. This mechanism has been suggested for Neurospora(see Rodriguez-Navarro, et al., supra) and recently also for root protoplasts, see Maathuis, et al, supra. For a stoichiometry in which uptake of one $K^+$ ion is energized by co-uptake of one proton, this high-affinity potassium-uptake mechanism has the capacity to accumulate potassium from solutions that contain as low as 27 nM $K^+$ (see equation, supra.). This estimate assumes physiological values for cytosolic $K^+$ activity of 100 $mM^3$, cytosolic pH of 7.4, external pH of 6, and a resting potential of $-150$ $mV^{18}$. $K^+$—$H^+$ co-uptake is therefore well-suited for the accumulation of $K^+$ into cells from dilute external $[K^+]$, thereby providing plants with adequate amounts of this mineral nutrient essential for growth.

High Na+ levels in soils and the ensuing Na+ influx into plants severely reduce agricultural production, with ≈30% of irrigated soils being affected by high [Na+]worldwide, see Greenway, et al., Annu. Rev. Plant Physiol. 31, 149–190 (1980). The molecular mechanisms of Na+-uptake into plants, however, remain unknown. In barley roots high-affinity Na+-uptake rates (Km ≈60 μM $Na^+$) in $K^+$-free media were ≈35% the rate of $K^+$-uptake at 200 μM 1, see Rains, et al., Plant Physiol. 42:314–318 (1967). These data correlate to findings presented here, showing that in the absence of $K^+$, HKT1 transports Na+ at ,≈26 ±10% the rate of $K^+$ (FIG. 1c, d). Furthermore, the large HKT1-mediated $Cs^+$-uptake currents (FIG. 1c, d) may contribute to the fact that $Cs^+$ is highly toxic to plant growth, see Sheahan, et al., Plant J. 3:647–656 (1993). $K^+$strongly competes with both $Na^+$- and $Cs^+$-uptake and $Cs^+$ toxicity in plant roots as shown by Rains, et al., supra, Welch, et al., Proc. Natl. Acad. Sci. USA 61:447–453 (1968), Sheahan, et al., supra, and Rains, et al., Plant Physiol. 42:314–318 (1967). Further investigation of HKT1 and HKT1 homologues can now be pursued to determine whether HKT1 genes contribute to environmentally and agriculturally significant $Na^+$ and $Cs^+$ toxicities in plants. The cloning and functional identification of HKT1 as a high-affinity $K^+$-uptake transporter will enable detailed molecular physiological and biophysical studies of potassium nutrition, potassium transport and related environmental stresses such as potassium deficiency and alkali metal toxicities in higher plants.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference.

What is claimed is:

1. A composition comprising an isolated polynucleotide encoding a high affinity potassium uptake transporter which polynucleotide hybridizes to SEQ. ID. No. 1 in a southern hybridization which includes washing at 65° C. with 0.2× SSC.

2. The composition of claim 1, wherein the polynucleotide is isolated from wheat.

3. The composition of claim 1, wherein the polynucleotide has a coding sequence as shown in SEQ. ID. No.1.

4. The composition of claim 1, wherein the polynucleotide encodes a polypeptide having a sequence as shown in SEQ. ID. No. 2.

5. A recombinant expression cassette comprising a promoter sequence operably linked to the polynucleotide of claim 1.

6. The expression cassette of claim 5, wherein the polynucleotide is operably linked to the promoter sequence in an antisense orientation.

7. The expression cassette of claim 5, wherein the promoter sequence is a constitutive.

8. The expression cassette of claim 5, wherein the polynucleotide is isolated from wheat.

9. The expression cassette of claim 5, wherein the polynucleotide is the coding sequence as shown in SEQ. ID. No. 1.

10. The expression cassette of claim 5, wherein the polynucleotide encodes a polypeptide having a sequence as shown in SEQ. ID. No. 2.

11. A plant comprising a heterologous recombinant expression cassette comprising a plant promoter sequence operably linked to the polynucleotide of claim 1.

12. The plant of claim 11, wherein the plant is a flowering plant.

13. The plant of claim 12, wherein the plant is wheat.

14. The plant of claim 11, wherein the polynucleotide is the coding sequence as shown in SEQ. ID. No. 1.

15. The plant of claim 11, wherein the polynucleotide encodes a polypeptide having a sequence as shown in SEQ. ID. No. 2.

16. The plant of claim 11, wherein the polynucleotide is operably linked to the promoter sequence in an antisense orientation.

17. A method of modulating alkali metal uptake in a plant, the method comprising introducing into the plant a recombinant expression cassette comprising a promoter sequence operably linked to the polynucleotide of claim 1.

18. The method of claim 17, wherein the plant is a flowering plant.

19. The method of claim 17, wherein the polynucleotide is operably linked to the promoter sequence in an antisense orientation.

20. The method of claim 17, wherein the polynucleotide is operably linked to the promoter sequence in a sense orientation.

21. A composition comprising an isolated polynucleotide encoding a high affinity potassium uptake transporter which has an amino acid sequence as shown in SEQ. ID. No. 2.

22. A plant comprising a heterologous recombinant expression cassette comprising a plant promoter sequence operably linked to the polynucleotide of claim 21.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 2016 base pairs
        ( B ) TYPE: nucleic acid
        ( C ) STRANDEDNESS: single
        ( D ) TOPOLOGY: linear     ( i i ) MOLECULE TYPE: DNA (genomic)

( i x ) FEATURE:
        ( A ) NAME/KEY: CDS
        ( B ) LOCATION: 37..1635

( x i ) SEQUENCE DESCRIPTION: SEQ ID NO:1:

```
AATTCGCATT TGTTTCTCAC ACTCATACAT AGCACC ATG GGC CGG GTG AAA AGA        54
                                       Met Gly Arg Val Lys Arg
                                       1               5

TTT TAC CAG GAT TTC ATC CAT ATC AAG CTG CAT AGC TTC TGC CGT ATC       102
Phe Tyr Gln Asp Phe Ile His Ile Lys Leu His Ser Phe Cys Arg Ile
            10                  15                  20

AGT GGA TAT GTT GTC GAT TCA ATA GCT TTT GTC TAT AGA TTT GTT GCA       150
Ser Gly Tyr Val Val Asp Ser Ile Ala Phe Val Tyr Arg Phe Val Ala
        25                  30                  35

TTG CAT GTT CAC CCC TTC TGG ATC CAA CTG TCC TAC TTC CTT GCC ATT       198
Leu His Val His Pro Phe Trp Ile Gln Leu Ser Tyr Phe Leu Ala Ile
    40                  45                  50

GCT ATA CTT GGT TCA GTC CTC TTG ATG TCG CTG AAA CCA AGC AAC CCT       246
```

|     |     |     |     |     |     |     |     |     |     |     |     |     |     |     |     |
|---|---|---|---|---|---|---|---|---|---|---|---|---|---|---|---|
| Ala | Ile | Leu | Gly | Ser | Val | Leu | Leu | Met | Ser | Leu | Lys | Pro | Ser | Asn | Pro |
| 55  |     |     |     |     | 60  |     |     |     | 65  |     |     |     |     |     | 70  |

| GAC | TTC | AGC | CCT | CCT | TAC | ATT | GAC | ATG | TTA | TTC | TTG | TCA | ACT | TCT | GCT | 294 |
|---|---|---|---|---|---|---|---|---|---|---|---|---|---|---|---|---|
| Asp | Phe | Ser | Pro | Pro | Tyr | Ile | Asp | Met | Leu | Phe | Leu | Ser | Thr | Ser | Ala |  |
|     |     |     |     | 75  |     |     |     |     | 80  |     |     |     |     | 85  |     |  |

| CTA | ACA | GTT | TCT | GGC | CTC | AGC | ACC | ATC | ACG | ATG | GAG | GAT | CTC | TCA | AGC | 342 |
|---|---|---|---|---|---|---|---|---|---|---|---|---|---|---|---|---|
| Leu | Thr | Val | Ser | Gly | Leu | Ser | Thr | Ile | Thr | Met | Glu | Asp | Leu | Ser | Ser |  |
|     |     |     | 90  |     |     |     |     | 95  |     |     |     |     | 100 |     |     |  |

| TCT | CAA | ATT | GTG | GTT | TTG | ACA | TTG | CTC | ATG | CTT | ATA | GGA | GGG | GAG | ATC | 390 |
|---|---|---|---|---|---|---|---|---|---|---|---|---|---|---|---|---|
| Ser | Gln | Ile | Val | Val | Leu | Thr | Leu | Leu | Met | Leu | Ile | Gly | Gly | Glu | Ile |  |
|     |     | 105 |     |     |     |     | 110 |     |     |     |     | 115 |     |     |     |  |

| TTT | GTT | TCA | CTC | TTA | GGG | CTC | ATG | CTT | AGA | GTG | AAC | CAT | CAA | GAC | ATG | 438 |
|---|---|---|---|---|---|---|---|---|---|---|---|---|---|---|---|---|
| Phe | Val | Ser | Leu | Leu | Gly | Leu | Met | Leu | Arg | Val | Asn | His | Gln | Asp | Met |  |
|     | 120 |     |     |     |     | 125 |     |     |     |     | 130 |     |     |     |     |  |

| CAA | GAT | CTT | CCA | AGC | GTG | AAG | ATC | AGC | TCG | GTT | CCT | GTC | GAG | CTT | GAA | 486 |
|---|---|---|---|---|---|---|---|---|---|---|---|---|---|---|---|---|
| Gln | Asp | Leu | Pro | Ser | Val | Lys | Ile | Ser | Ser | Val | Pro | Val | Glu | Leu | Glu |  |
| 135 |     |     |     |     | 140 |     |     |     |     | 145 |     |     |     |     | 150 |  |

| GAG | CTA | GAC | TTG | CCC | AAC | AGC | ATG | GCA | CTA | TGT | GAT | GAG | TCG | CAG | CTT | 534 |
|---|---|---|---|---|---|---|---|---|---|---|---|---|---|---|---|---|
| Glu | Leu | Asp | Leu | Pro | Asn | Ser | Met | Ala | Leu | Cys | Asp | Glu | Ser | Gln | Leu |  |
|     |     |     |     | 155 |     |     |     |     | 160 |     |     |     |     | 165 |     |  |

| GAA | GAA | GCA | GCT | CAT | GCA | ATT | CCA | CCC | AAG | AAA | TGT | ACA | GAG | TTG | AAG | 582 |
|---|---|---|---|---|---|---|---|---|---|---|---|---|---|---|---|---|
| Glu | Glu | Ala | Ala | His | Ala | Ile | Pro | Pro | Lys | Lys | Cys | Thr | Glu | Leu | Lys |  |
|     |     |     |     | 170 |     |     |     |     | 175 |     |     |     |     | 180 |     |  |

| AGG | AGT | AGG | TCT | GTC | AAG | TGC | TTA | GGA | TAT | GTG | GTC | TTT | GGG | TAC | TTT | 630 |
|---|---|---|---|---|---|---|---|---|---|---|---|---|---|---|---|---|
| Arg | Ser | Arg | Ser | Val | Lys | Cys | Leu | Gly | Tyr | Val | Val | Phe | Gly | Tyr | Phe |  |
|     |     |     | 185 |     |     |     |     | 190 |     |     |     |     | 195 |     |     |  |

| GCC | ATG | ATC | CAT | GTC | TTG | GGC | TTT | CTG | CTG | GTT | TTT | CTG | TAT | ATA | ACT | 678 |
|---|---|---|---|---|---|---|---|---|---|---|---|---|---|---|---|---|
| Ala | Met | Ile | His | Val | Leu | Gly | Phe | Leu | Leu | Val | Phe | Leu | Tyr | Ile | Thr |  |
|     |     | 200 |     |     |     |     | 205 |     |     |     |     | 210 |     |     |     |  |

| CAT | GTG | CCA | ACT | GCA | AGT | GCC | CCA | CTG | AAC | AAG | AAA | GGG | ATC | AAC | ATC | 726 |
|---|---|---|---|---|---|---|---|---|---|---|---|---|---|---|---|---|
| His | Val | Pro | Thr | Ala | Ser | Ala | Pro | Leu | Asn | Lys | Lys | Gly | Ile | Asn | Ile |  |
| 215 |     |     |     |     | 220 |     |     |     |     | 225 |     |     |     |     | 230 |  |

| GTG | CTC | TTC | TCA | CTA | TCA | GTC | ACC | GTT | GCC | TCC | TGT | GCG | AAT | GCA | GGA | 774 |
|---|---|---|---|---|---|---|---|---|---|---|---|---|---|---|---|---|
| Val | Leu | Phe | Ser | Leu | Ser | Val | Thr | Val | Ala | Ser | Cys | Ala | Asn | Ala | Gly |  |
|     |     |     |     | 235 |     |     |     |     | 240 |     |     |     |     | 245 |     |  |

| CTC | GTG | CCC | ACA | AAT | GAG | AAC | ATG | GTC | ATC | TTC | TCA | AAG | AAT | TCA | GGC | 822 |
|---|---|---|---|---|---|---|---|---|---|---|---|---|---|---|---|---|
| Leu | Val | Pro | Thr | Asn | Glu | Asn | Met | Val | Ile | Phe | Ser | Lys | Asn | Ser | Gly |  |
|     |     |     |     | 250 |     |     |     |     | 255 |     |     |     |     | 260 |     |  |

| CTC | TTG | TTG | CTG | CTG | AGT | GGC | CAG | ATG | CTC | GCA | GGC | AAT | ACA | TTG | TTC | 870 |
|---|---|---|---|---|---|---|---|---|---|---|---|---|---|---|---|---|
| Leu | Leu | Leu | Leu | Leu | Ser | Gly | Gln | Met | Leu | Ala | Gly | Asn | Thr | Leu | Phe |  |
|     |     | 265 |     |     |     |     | 270 |     |     |     |     | 275 |     |     |     |  |

| CCT | CTC | TTC | CTG | AGG | CTA | CTG | GTG | TGG | TTC | CTG | GGG | AGG | ATC | ACA | AAG | 918 |
|---|---|---|---|---|---|---|---|---|---|---|---|---|---|---|---|---|
| Pro | Leu | Phe | Leu | Arg | Leu | Leu | Val | Trp | Phe | Leu | Gly | Arg | Ile | Thr | Lys |  |
|     | 280 |     |     |     |     | 285 |     |     |     |     | 290 |     |     |     |     |  |

| GTG | AAG | GAG | CTG | AGG | CTC | ATG | ATC | AAT | AAC | CCC | GAG | GAA | GTG | CGT | TTT | 966 |
|---|---|---|---|---|---|---|---|---|---|---|---|---|---|---|---|---|
| Val | Lys | Glu | Leu | Arg | Leu | Met | Ile | Asn | Asn | Pro | Glu | Glu | Val | Arg | Phe |  |
| 295 |     |     |     |     | 300 |     |     |     |     | 305 |     |     |     |     | 310 |  |

| GCT | AAT | TTG | CTT | GCT | AGG | TTG | CCA | ACT | GTG | TTT | CTC | TCC | TCA | ACG | GTC | 1014 |
|---|---|---|---|---|---|---|---|---|---|---|---|---|---|---|---|---|
| Ala | Asn | Leu | Leu | Ala | Arg | Leu | Pro | Thr | Val | Phe | Leu | Ser | Ser | Thr | Val |  |
|     |     |     |     | 315 |     |     |     |     | 320 |     |     |     |     | 325 |     |  |

| GTT | GGC | CTT | GTA | GCA | GCT | GGG | GTC | ACG | ATG | TTC | TGC | GCT | GTT | GAT | TGG | 1062 |
|---|---|---|---|---|---|---|---|---|---|---|---|---|---|---|---|---|
| Val | Gly | Leu | Val | Ala | Ala | Gly | Val | Thr | Met | Phe | Cys | Ala | Val | Asp | Trp |  |
|     |     |     | 330 |     |     |     |     | 335 |     |     |     |     | 340 |     |     |  |

| AAT | TCT | TCA | GTC | TTT | GAT | GGG | CTC | AGC | TCT | TAT | CAG | AAG | ACT | GTC | AAT | 1110 |
|---|---|---|---|---|---|---|---|---|---|---|---|---|---|---|---|---|
| Asn | Ser | Ser | Val | Phe | Asp | Gly | Leu | Ser | Ser | Tyr | Gln | Lys | Thr | Val | Asn |  |
|     |     | 345 |     |     |     |     | 350 |     |     |     |     | 355 |     |     |     |  |

| GCA | TTC | TTC | ATG | GTG | GTG | AAT | GCG | AGG | CAC | TCA | GGG | GAG | AAT | TCC | ATC | 1158 |
|---|---|---|---|---|---|---|---|---|---|---|---|---|---|---|---|---|
| Ala | Phe | Phe | Met | Val | Val | Asn | Ala | Arg | His | Ser | Gly | Glu | Asn | Ser | Ile |  |
|     |     | 360 |     |     |     |     | 365 |     |     |     |     | 370 |     |     |     |  |

| GAC | TGC | TCG | CTC | ATG | TCC | CCT | GCC | ATT | ATA | GTA | CTA | TTC | ATC | GTC | ATG | 1206 |

```
Asp Cys Ser Leu Met Ser Pro Ala Ile Ile Val Leu Phe Ile Val Met
375             380                 385                 390

ATG TAT TTG CCA TCA TCA GCA ACA TTT GCA CCA CCC AGT GGA GAT ACT      1254
Met Tyr Leu Pro Ser Ser Ala Thr Phe Ala Pro Pro Ser Gly Asp Thr
                395                 400                 405

AAA ACC ACC AAT GAG AAC ACG AAA GGG AAA GTC AAG AGA GGG TCG TTG      1302
Lys Thr Thr Asn Glu Asn Thr Lys Gly Lys Val Lys Arg Gly Ser Leu
                410                 415                 420

GTG CAG AAT TTG GCA TTC TCA CCG CTC GGG TGT AAC ATC ATC TTT GTG      1350
Val Gln Asn Leu Ala Phe Ser Pro Leu Gly Cys Asn Ile Ile Phe Val
            425                 430                 435

ATG GTT GCC TGC ATC ACG GAA AGG AGA AGG CTC AGA AAC GAT CCA CTC      1398
Met Val Ala Cys Ile Thr Glu Arg Arg Arg Leu Arg Asn Asp Pro Leu
    440                 445                 450

AAC TTC TCC ACC TTG AAC ATG ATA TTT GAG GTC ATC AGC GCA TAT GGC      1446
Asn Phe Ser Thr Leu Asn Met Ile Phe Glu Val Ile Ser Ala Tyr Gly
455                 460                 465                 470

AAT GCA GGG TTA TCC ACT GGT TAC AGT TGT TCT AGA CTG CAT CAG CTG      1494
Asn Ala Gly Leu Ser Thr Gly Tyr Ser Cys Ser Arg Leu His Gln Leu
                475                 480                 485

CAC CCA GAG ATC ATC TGC CAG GAC AAA CCA TAC AGC TTT TCT GGA TGG      1542
His Pro Glu Ile Ile Cys Gln Asp Lys Pro Tyr Ser Phe Ser Gly Trp
                490                 495                 500

TGG AGT GAC GGA GGA AAG TTT GTG CTA ATA TTG GTC ATG CTC TAT GGA      1590
Trp Ser Asp Gly Gly Lys Phe Val Leu Ile Leu Val Met Leu Tyr Gly
            505                 510                 515

AGG CTT AAG GCT TTC ACA CTG GCC ACG GGT AAA TCC TGG AAA GTA          1635
Arg Leu Lys Ala Phe Thr Leu Ala Thr Gly Lys Ser Trp Lys Val
        520                 525                 530

TGATACAAGT GGCCAAGATT ACTTGGAAAG GCAGATGTAC CAAATTGGTA TAACTGTCGC   1695

TAGTGTACTG CCTGAAGAAT CAGGCTTCTA ATTGGATTAT AGTTTGTGGA TGTTGCGCTT   1755

GCAAAGGACA AGCTTCTGTT TCCCTGCTAA AGTCATCTTT GTATTGTCA GTCATCATCA    1815

GGTATCAATG CAACTGAAGA ATTGAGCCAT CTGTTGATGT GTTGCATGCT AGATGTAACC   1875

ACATGAGTTC CCCACAATTG TAGCGAAAGA GAAAGCAAAT ATTATTTGTA TTGTTGGAGT   1935

GGAGTTAATA TTATTGCACA CAATTTATAA TACAGATAAA TTTTGTGTTG CTTAAAAAAA   1995

AAAAAAAAAA AAAAAAAAAA A                                             2016
```

(2) INFORMATION FOR SEQ ID NO:2:

(i) SEQUENCE CHARACTERISTICS:
        (A) LENGTH: 533 amino acids
        (B) TYPE: amino acid
        (D) TOPOLOGY: linear     (ii) MOLECULE TYPE: protein     (xi) SEQUENCE DESCRIPTION: SEQ ID NO:2:

```
Met Gly Arg Val Lys Arg Phe Tyr Gln Asp Phe Ile His Ile Lys Leu
1               5                   10                  15

His Ser Phe Cys Arg Ile Ser Gly Tyr Val Val Asp Ser Ile Ala Phe
                20                  25                  30

Val Tyr Arg Phe Val Ala Leu His Val His Pro Phe Trp Ile Gln Leu
            35                  40                  45

Ser Tyr Phe Leu Ala Ile Ala Ile Leu Gly Ser Val Leu Leu Met Ser
        50                  55                  60

Leu Lys Pro Ser Asn Pro Asp Phe Ser Pro Pro Tyr Ile Asp Met Leu
65                  70                  75                  80
```

```
Phe Leu Ser Thr Ser Ala Leu Thr Val Ser Gly Leu Ser Thr Ile Thr
                85              90                  95

Met Glu Asp Leu Ser Ser Ser Gln Ile Val Val Leu Thr Leu Leu Met
            100             105             110

Leu Ile Gly Gly Glu Ile Phe Val Ser Leu Leu Gly Leu Met Leu Arg
        115             120             125

Val Asn His Gln Asp Met Gln Asp Leu Pro Ser Val Lys Ile Ser Ser
    130             135             140

Val Pro Val Glu Leu Glu Glu Leu Asp Leu Pro Asn Ser Met Ala Leu
145             150             155                         160

Cys Asp Glu Ser Gln Leu Glu Glu Ala Ala His Ala Ile Pro Pro Lys
                165             170             175

Lys Cys Thr Glu Leu Lys Arg Ser Arg Ser Val Lys Cys Leu Gly Tyr
            180             185             190

Val Val Phe Gly Tyr Phe Ala Met Ile His Val Leu Gly Phe Leu Leu
        195             200             205

Val Phe Leu Tyr Ile Thr His Val Pro Thr Ala Ser Ala Pro Leu Asn
    210             215             220

Lys Lys Gly Ile Asn Ile Val Leu Phe Ser Leu Ser Val Thr Val Ala
225             230             235                         240

Ser Cys Ala Asn Ala Gly Leu Val Pro Thr Asn Glu Asn Met Val Ile
                245             250             255

Phe Ser Lys Asn Ser Gly Leu Leu Leu Leu Leu Ser Gly Gln Met Leu
            260             265             270

Ala Gly Asn Thr Leu Phe Pro Leu Phe Leu Arg Leu Leu Val Trp Phe
        275             280             285

Leu Gly Arg Ile Thr Lys Val Lys Glu Leu Arg Leu Met Ile Asn Asn
    290             295             300

Pro Glu Glu Val Arg Phe Ala Asn Leu Leu Ala Arg Leu Pro Thr Val
305             310             315                         320

Phe Leu Ser Ser Thr Val Val Gly Leu Ala Ala Gly Val Thr Met
                325             330             335

Phe Cys Ala Val Asp Trp Asn Ser Ser Val Phe Asp Gly Leu Ser Ser
            340             345             350

Tyr Gln Lys Thr Val Asn Ala Phe Phe Met Val Val Asn Ala Arg His
        355             360             365

Ser Gly Glu Asn Ser Ile Asp Cys Ser Leu Met Ser Pro Ala Ile Ile
    370             375             380

Val Leu Phe Ile Val Met Met Tyr Leu Pro Ser Ser Ala Thr Phe Ala
385             390             395                         400

Pro Pro Ser Gly Asp Thr Lys Thr Thr Asn Glu Asn Thr Lys Gly Lys
                405             410             415

Val Lys Arg Gly Ser Leu Val Gln Asn Leu Ala Phe Ser Pro Leu Gly
            420             425             430

Cys Asn Ile Ile Phe Val Met Val Ala Cys Ile Thr Glu Arg Arg Arg
        435             440             445

Leu Arg Asn Asp Pro Leu Asn Phe Ser Thr Leu Asn Met Ile Phe Glu
    450             455             460

Val Ile Ser Ala Tyr Gly Asn Ala Gly Leu Ser Thr Gly Tyr Ser Cys
465             470             475                         480

Ser Arg Leu His Gln Leu His Pro Glu Ile Ile Cys Gln Asp Lys Pro
                485             490             495

Tyr Ser Phe Ser Gly Trp Trp Ser Asp Gly Gly Lys Phe Val Leu Ile
            500             505             510
```

```
Leu  Val  Met  Leu  Tyr  Gly  Arg  Leu  Lys  Ala  Phe  Thr  Leu  Ala  Thr  Gly
          515                 520                           525

Lys  Ser  Trp  Lys  Val
          530
```